(12) United States Patent
Cude

(10) Patent No.: US 8,572,834 B2
(45) Date of Patent: Nov. 5, 2013

(54) METHOD OF LOCKING A SYRINGE TO AN INJECTOR

(75) Inventor: J. Michael Cude, College Grove, TN (US)

(73) Assignee: Coeur, Inc., Lebanon, TN (US)

( * ) Notice: Subject to any disclaimer, the term of this patent is extended or adjusted under 35 U.S.C. 154(b) by 175 days.

(21) Appl. No.: 13/195,525

(22) Filed: Aug. 1, 2011

(65) Prior Publication Data

US 2011/0283510 A1   Nov. 24, 2011

Related U.S. Application Data

(62) Division of application No. 10/544,950, filed as application No. PCT/IB2004/050493 on Apr. 22, 2004, now Pat. No. 7,988,684.

(60) Provisional application No. 60/466,893, filed on Apr. 30, 2003.

(51) Int. Cl.
   *B21D 39/00*   (2006.01)
   *A61M 25/16*   (2006.01)

(52) U.S. Cl.
   USPC ............... 29/525.01; 29/525.02; 604/154

(58) Field of Classification Search
   USPC .............. 29/525.01, 525.02; 604/533, 154
   See application file for complete search history.

(56) References Cited

U.S. PATENT DOCUMENTS

| | | | |
|---|---|---|---|
| 5,300,031 A | 4/1994 | Neer et al. | |
| 5,865,805 A | 2/1999 | Ziemba | |
| 5,913,844 A | 6/1999 | Ziemba et al. | |
| 5,997,502 A | 12/1999 | Reilly et al. | |
| 6,080,136 A | 6/2000 | Trull et al. | |
| 6,090,064 A | 7/2000 | Reilly et al. | |
| 6,312,410 B1 | 11/2001 | Yamamoto | |
| 6,336,913 B1 | 1/2002 | Spohn et al. | |
| 6,402,717 B1 | 6/2002 | Reilly et al. | |
| 6,402,718 B1 | 6/2002 | Reilly et al. | |
| 6,475,192 B1 | 11/2002 | Reilly et al. | |

(Continued)

FOREIGN PATENT DOCUMENTS

WO   03/020346 A2   3/2003

OTHER PUBLICATIONS

European Search Report for 04728884 dated Aug. 6, 2007, 3 pgs.

(Continued)

*Primary Examiner* — Jermie Cozart
(74) *Attorney, Agent, or Firm* — Hahn, Loeser & Parks, LLP

(57) ABSTRACT

A syringe adapter assembly 10 for permitting a front loadable power injector 100 having a pressure jacket 106 with an open front end to attach syringes 70 that do not require pressure jackets for their intended purpose. The syringe adapter assembly comprises a main adapter body 12 having a central bore 28 therethrough, a lifting ring 60 secured within the main adapter body 12, a connector plate 50 for attaching the main adapter body to the door injector, and a drive ram extender 30 that attaches to the drive ram. Additionally, the ram extender 30 may have a ram tip cone 40 attached at its forward end. The connector plate 50 is inserted into a recess 112 in the rear side of the door, and attaches to the main adapter body 12 located on the front side of the door. The invention additionally or alternatively comprises both a syringe lock 120 that locks an installed syringe relative to the injector to prevent unwanted movement of the syringe, and a method of locking syringe relative to an injector.

13 Claims, 14 Drawing Sheets

(56) References Cited

U.S. PATENT DOCUMENTS

| | | |
|---|---|---|
| 6,659,979 B2 | 12/2003 | Neer et al. |
| 6,716,195 B2 | 4/2004 | Nolan, Jr. et al. |
| 6,733,478 B2 | 5/2004 | Reilly et al. |
| 6,764,466 B1 | 7/2004 | Staats et al. |
| 6,821,013 B2 | 11/2004 | Reilly et al. |
| 7,029,458 B2 | 4/2006 | Spohn et al. |
| 7,081,104 B2 | 7/2006 | Neer et al. |

OTHER PUBLICATIONS

PCT/IB2004/050493 International Search Report dated Jul. 14, 2005, 3 pgs.

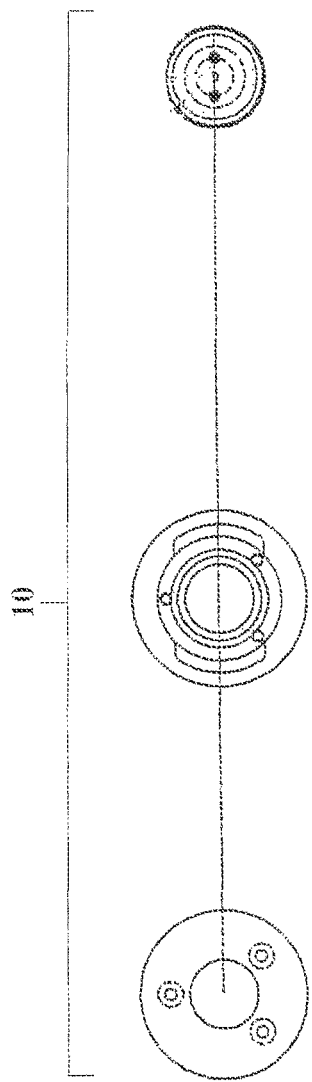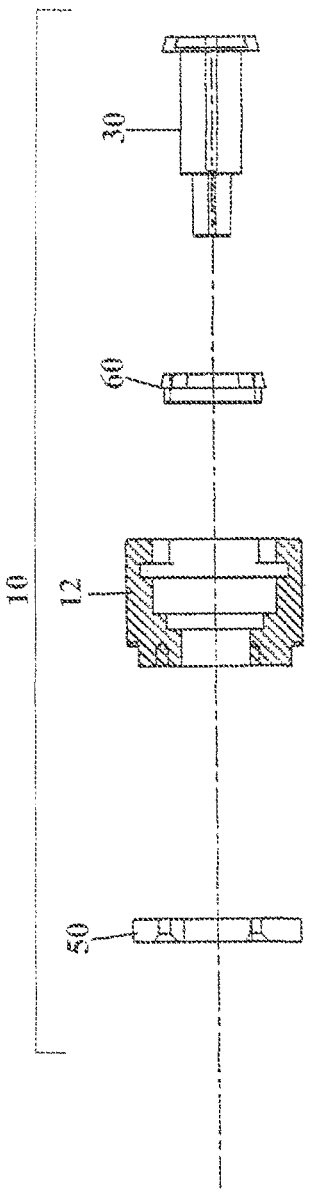

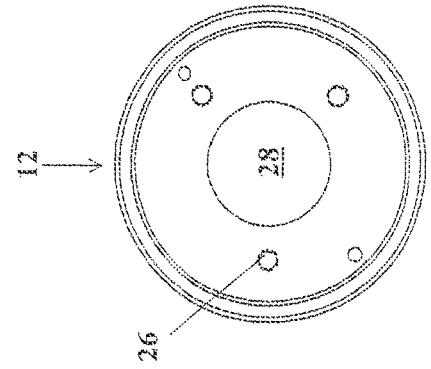
FIG. 10
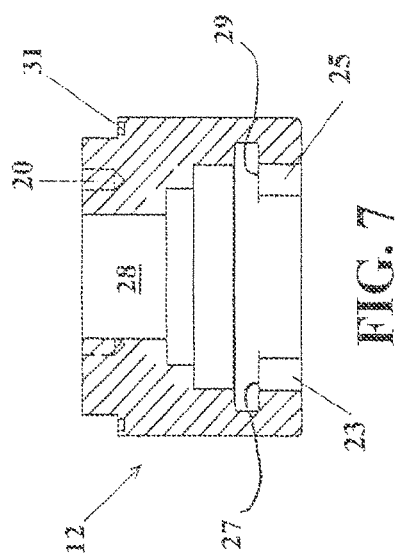
FIG. 9
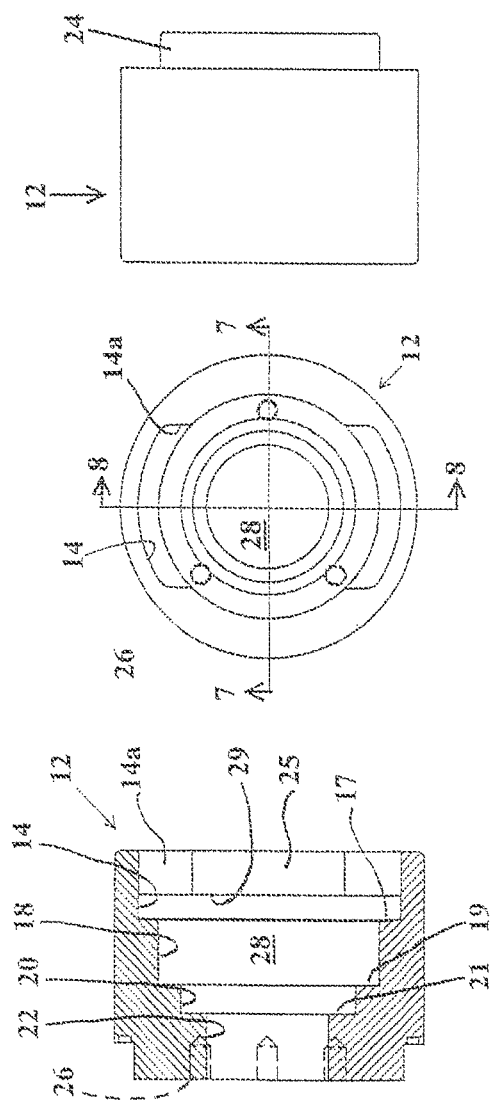
FIG. 7
FIG. 6
FIG. 8

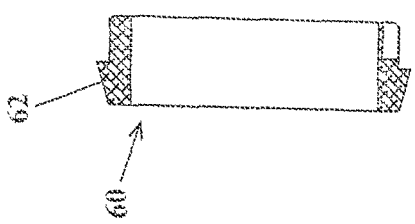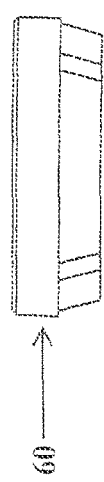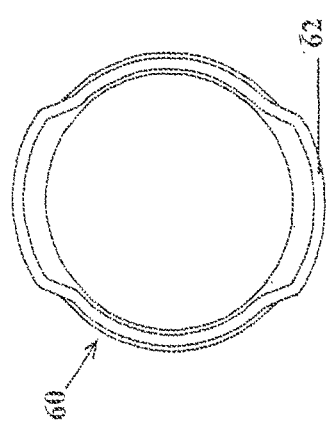

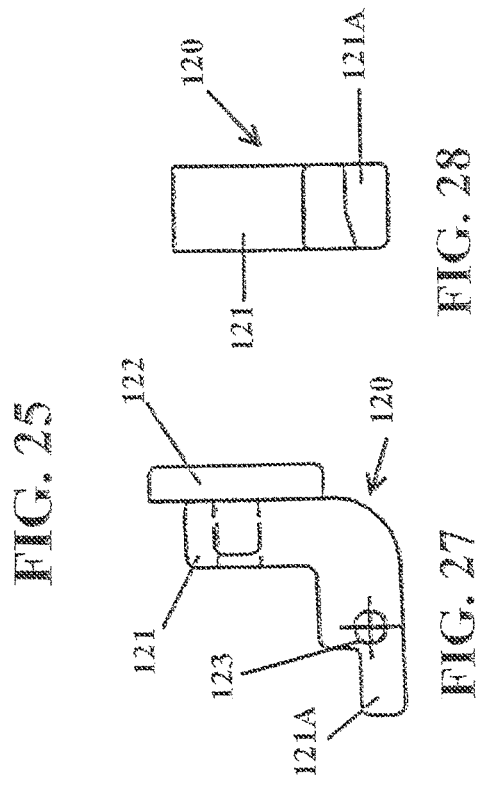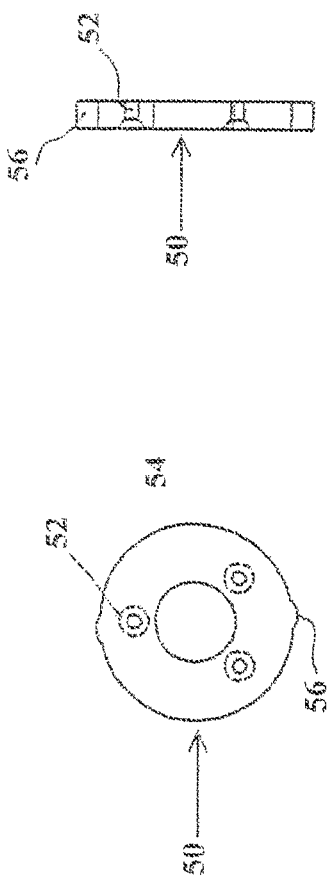

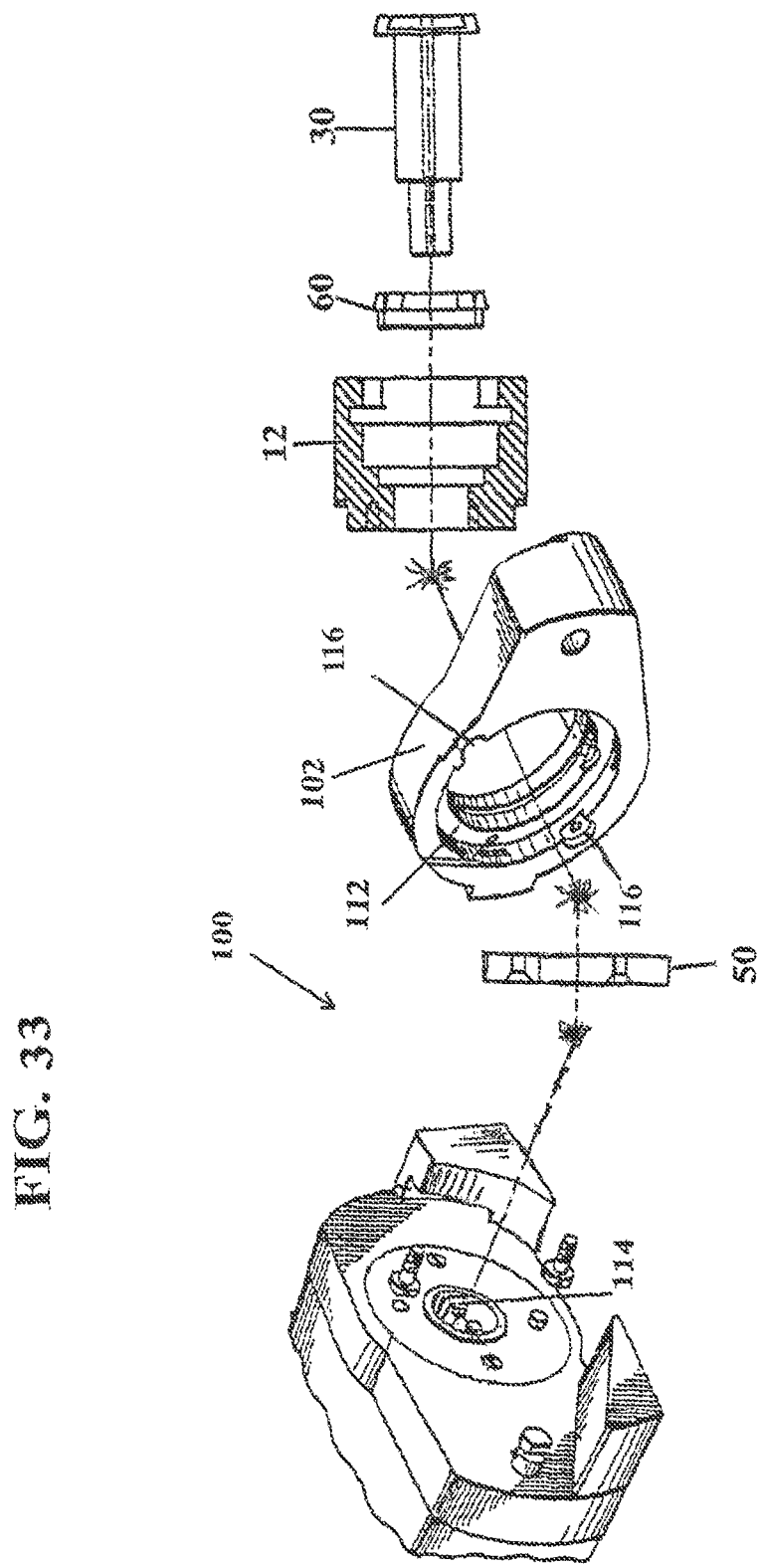

METHOD OF LOCKING A SYRINGE TO AN INJECTOR

CROSS-REFERENCE TO RELATED APPLICATIONS

This U.S. patent application is a divisional application of and claims the benefit of U.S. patent application Ser. No. 10/554,950 filed on Oct. 9, 2006, now published as U.S. Patent Publication No. 2007/0052409, which claims the benefit of PCT International Application No. PCT/IB04/50493 filed on Apr. 22, 2004, which claims the benefit of U.S. Provisional Patent Application Ser. No. 60/466,893 filed on Apr. 30, 2003, all of which are herein incorporated by reference in their entirety.

TECHNICAL FIELD

This invention generally relates to power-driven contrast injectors, and specifically to an adapter and syringe for use with a power injector.

BACKGROUND OF THE INVENTION

In the field of contrast injection, a contrast medium of suitable indicating character (radiopacity) is introduced in a person or animal's body. To effect the introduction of the contrast medium into the patient's body, a syringe may be machine-mounted in a so-called "power injector" apparatus, with the distal end of the syringe being connected to the catheter which is introduced into the patient.

Injectors are devices that expel fluid, such as contrast media, from a syringe and through a tube into a person or animal. The injectors are provided with an injector unit, usually adjustably fixed to a stand or support, and have a drive ram that couples to the plunger of the syringe to drive it forward to expel fluid into the tube, or to drive the plunger rearward to draw fluid into the syringe to fill it. Usually the syringe is a disposable replacement type.

U.S. Pat. No. 5,300,031 discloses a front-loading injector ("the '031 injector"). The '031 injector has a pressure jacket mounted to its front face for receiving a closely-fitting syringe. A syringe having an open back end is inserted into the pressure jacket and coupled to the open end of the pressure jacket by a rotating motion. This same rotating motion causes the plunger in the syringe to couple to the end of the ram. The pressure jacket supports the side walls of the syringe against injection pressure during operation of the injector. After an injection, a reverse rotating motion unlocks the syringe from the pressure jacket and releases the plunger from the ram, so the syringe can be removed and replaced.

One problem with the '031 injector is that the pressure jacket limits the types of syringes that can be used with the '031 injector. Syringes that do not need pressure jackets cannot be utilized. Another problem with the '031 injector is that the ram-plunger connection comprises complex moving parts that require periodic maintenance and are prone to needing repair to function properly. A third problem with the '031 injector is that the combination pressure jacket and syringe make it difficult to view the contrast media inside the syringe, for example to determine whether air bubbles are present within the syringe.

U.S. Pat. No. 6,080,136 discloses a front-loading syringe and adapter for a contrast injector. The syringe comprises a one-piece barrel and open back end such that the syringe can be front loaded onto an injector equipped with the disclosed adapter. The syringe barrel is transparent and does not require the use of a pressure jacket for its intended use. Therefore, the contrast media inside the syringe can be easily viewed and inspected for the presence of air bubbles.

An additional problem with injectors and syringe adapters that attach a syringe via insertion and rotation of the syringe into the adapter or injector is that the syringe could rotate in the injector or adapter and cause the syringe to not be fully installed during an injection, which is more likely to result in the syringe being misaligned, which could result in fluid spillage.

Accordingly, the present invention is hereby submitted.

BRIEF SUMMARY OF THE INVENTION

One aspect of the invention is a syringe adapter assembly for a front-loading power injector having a front door with an opening therethrough and a recess in a rear portion of the front door that surrounds the front door opening, the adapter assembly comprising: an adapter body having central bore therethrough, a front end that is adapted to engage a syringe, and a rear portion that is sized to be received at least partially within the front door opening, the rear portion having a plurality of axially-extending threaded apertures therein; and a rear connector plate adapted to be received within the recess in the rear portion of the front door, the rear connector plate having a plurality of apertures therethrough that correspond to the axially-extending adapter body apertures.

A second aspect of the invention is a syringe adapter for attaching a syringe to a power injector, comprising an adapter body having a central bore therethrough, a rear end attachable to the injector, and a front end having an interior shoulder and diametrally opposed retaining flanges spaced forwardly from the shoulder to form a groove that receives a portion of a syringe upon insertion of a rear end of the syringe into the adapter and rotation of the syringe, and a syringe lock to retain an engaged syringe in a substantially fixed position relative to the adapter body.

A third aspect of the invention is a method of locking a syringe relative to a front-loadable power injector, the method comprising the steps of: providing a syringe having mounting flanges proximate to a rear end of the syringe; providing a front-loadable injector having a syringe receiving opening and a pair of retaining flanges adapted to engage the syringe mounting flanges upon rearward insertion of the syringe within the opening and rotation of the syringe; providing a syringe lock at least partially comprising a detent in a rotational path of the syringe; and installing a syringe relative to the injector by engaging the syringe mounting flanges with the injector retaining flanges.

BRIEF SUMMARY OF THE DRAWINGS

FIG. 4 is a schematic view of the components of the syringe adapter assembly.

FIG. 5 is a side exploded view of the components of the syringe adapter assembly.

FIG. 6 is a front view of a first preferred embodiment of a syringe adapter body, in accordance with an embodiment of the present invention.

FIG. 7 is a side cross-sectional view of the syringe adapter body, taken along line 7-7 of FIG. 6.

FIG. 8 is a side cross-sectional view of the syringe adaptor body, taken along line 8-8 of FIG. 6.

FIG. 9 is a side elevational view of the syringe adaptor body shown in FIG. 6.

FIG. 10 is a rear view of the syringe adaptor body shown in FIG. 6.

FIG. 17 is a side elevational view of a lifting ring.

FIG. 18 is a back view of the lifting ring shown in FIG. 17.

FIG. 19 is a side elevational view of the lifting ring relative to FIG. 17.

FIG. 20 is a front view of the lifting ring shown in FIG. 17.

FIG. 21 is a side cross-sectional view of the lifting ring.

FIG. 22 is a side cross-sectional view of the lifting ring taken 90 degrees from FIG. 21.

FIG. 24 is a top plan view of a syringe connector plate.

FIG. 25 is a side view of a syringe connector plate shown in FIG. 24.

FIG. 26 is a rear view of a connector plate shown in FIG. 24 without apertures.

FIG. 27 is a front view of a portion of an embodiment of a syringe lock.

FIG. 28 is side view of the portion of the syringe lock shown in FIG. 27.

FIG. 33 is a schematic exploded view showing the syringe adapter assembly of FIG. 5 attached to the injector head of FIG. 2.

DETAILED DESCRIPTION

Figure 1:
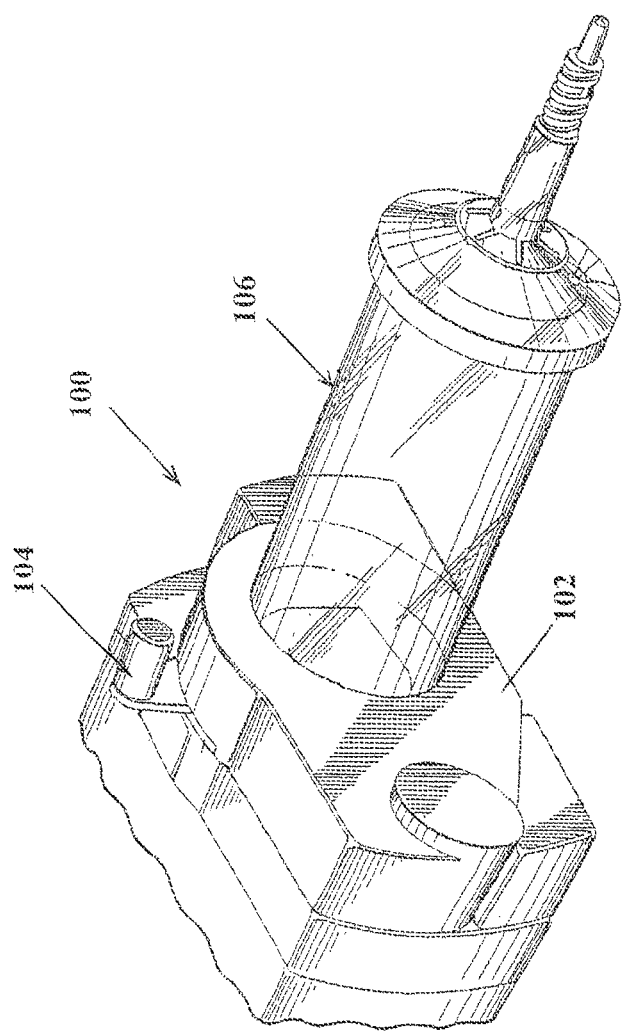
FIG. 1 is a perspective view of a portion of an injector head as disclosed in U.S. Pat. No. 5,300,031.
Figure 2:
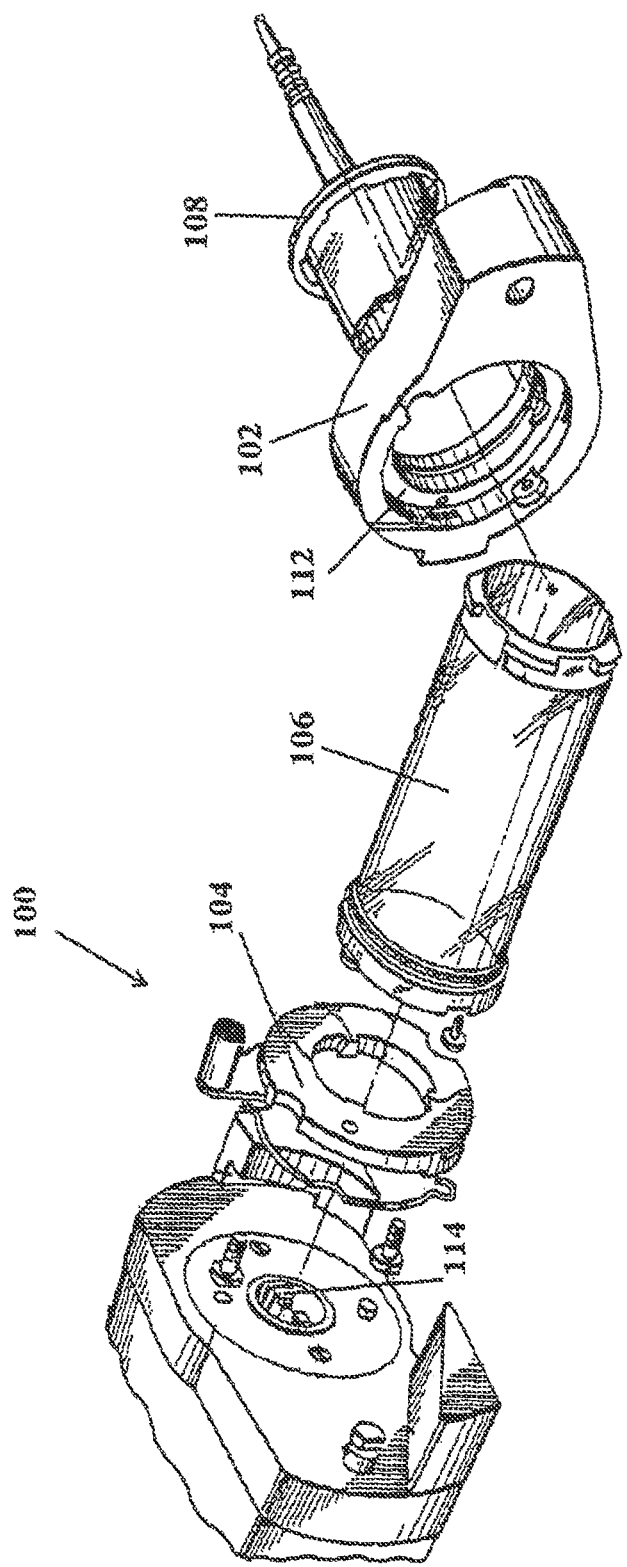
FIG. 2 is an exploded perspective view of the injector head of FIG. 1.
Figure 3:
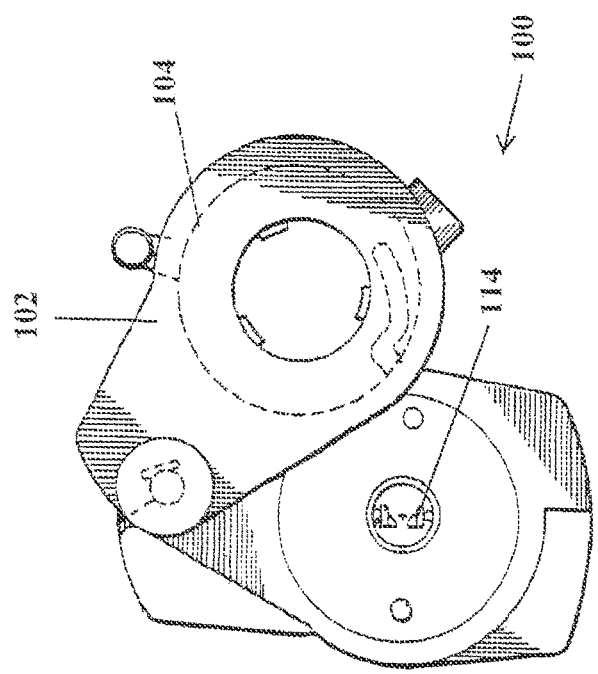
FIG. 3 is a front view of the injector of FIG. 1, with the door in an opened position.

A perspective view of a prior art front-loading injector for use with the present invention is illustrated in FIG. 1. The injector, presently known as a CT9000® and manufactured by Liebel-Flarsheim, Inc., comprises a power head 100, a rotatable door 102, and pressure jacket 106. The pressure jacket 106 has an open front end that receives the rearward end of a syringe 108 (see FIG. 2). FIG. 2 illustrates an exploded view of the injector head 100. Rotating cam assembly 104 is received in shoulder 112 of door 102 when installed. FIG. 3 illustrates a front view of the injector head of FIG. 1, with the door opened to provide access to the ram.

A preferred embodiment of a syringe adapter assembly 10 is illustrated in FIGS. 4-5. The syringe adapter assembly 10 comprises an adapter body 12, a lifting ring 60, ram extender 30, and syringe connector plate 50.

A preferred embodiment of syringe adapter body 12 is illustrated in FIGS. 6-10. The outer surface of the adapter body 12 is preferably cylindrical, although the outer surface may be any of a plurality of shapes without deviating from the scope of the present invention. The adapter body 12 has mounted thereon or integrally formed therewith a rear cylindrical extension 24. An o-ring 31 may be positioned at the junction of adapter body 12 and rear cylindrical extension 24. A central bore 28 extends through the adapter body 12. The central bore 28 receives a ram extender 30, illustrated in FIGS. 12-13, which is coupled to the drive ram of the injector. The central bore 28 is bound in the rear cylindrical extension 24 by first bounding wall 22. First bounding wall 22 extends forwardly from the rear cylindrical extension 24. Without the lifting ring 60 mounted in the adapter body 12, the first bounding wall 22 terminates at shoulder 21. The lifting ring 60, illustrated in FIGS. 17-22, mounts within the area defined by shoulder 21 and lifting ring bounding wall 20. The interior diameter of lifting ring 40 is substantially equal to the first bounding wall 22. As such, when the lifting ring 40 is mounted within adapter body 12, the first bounding wall 22 operably extends to shoulder 19.

The central bore 28 is also bound in the main body by second bounding wall 18 and by third bounding wall 14. The first bounding wall 22 is of smaller diameter than second bounding wall 18, and the second bounding wall 18 is of smaller diameter than third bounding wall 14.

The adapter includes front slot opening 14a communicating with the third bounding wall 14 of central bore 28 and forming therewith diametrally opposed grooves 27 and 29, and thereby defining diametrally opposed retention flange portions 23 and 25 transverse to the slot opening, for engagement with a syringe, as described below.

As used herein, the term "diametrally opposed" means that the relevant structural elements are located at opposite sides of a cylindrical or circular element or member of the appertaining apparatus. The diametrally opposed elements or members are thus symmetrically arranged with respect to an associated diameter of the cylindrical or circular part or structure with which they are associated.

Figure 11:
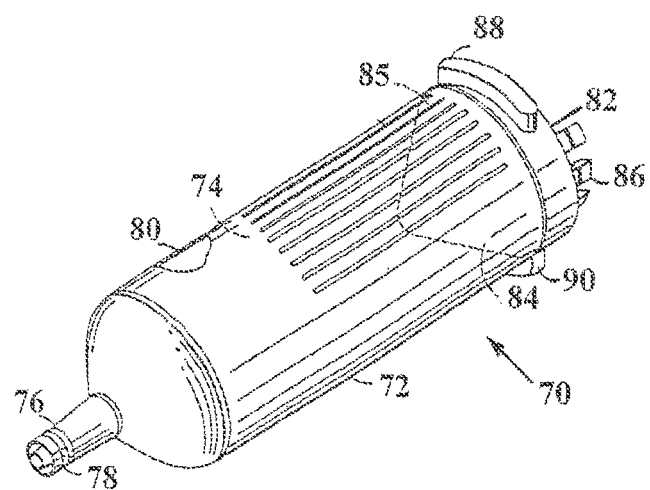
FIG. 11 is a perspective view of a syringe for use with the syringe adapter assembly.
Figure 12D:
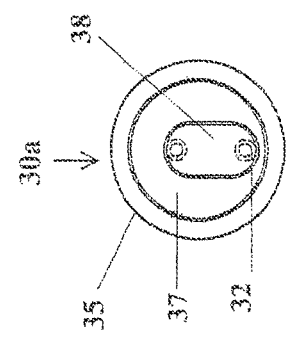
FIG. 12D is a back view of the ram extender shown in FIG. 12A.
Figure 12C:
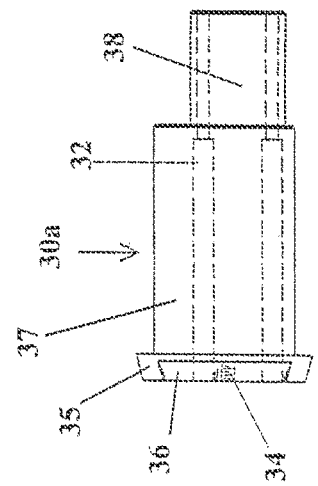
FIG. 12C is a side view of the ram extender shown in FIG. 12A.
Figure 12A:
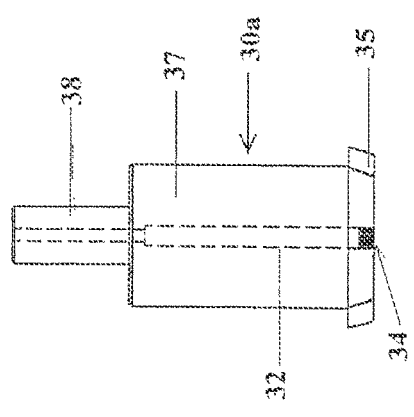
FIG. 12A is a side view of a first embodiment of a ram extender.
Figure 12B:
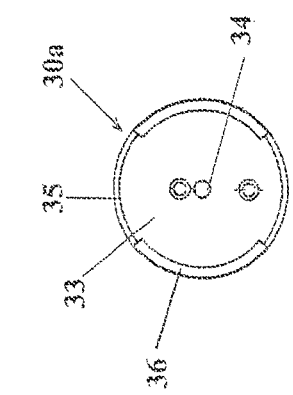
FIG. 12B is a front view of the ram extender shown in FIG. 12A.
Figure 13D:
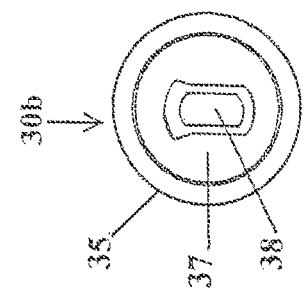
FIG. 13D is a back view of the ram extender shown in FIG. 13A.
Figure 13C:
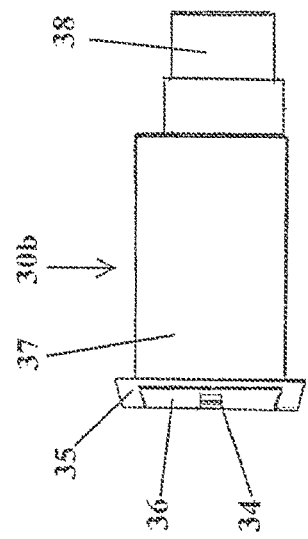
FIG. 13C is a right side view of the ram extender shown in FIG. 13A.
Figure 13A:
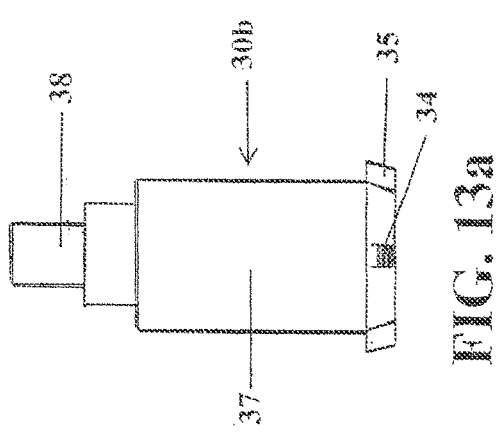
FIG. 13A is a side view of a second embodiment of a ram extender.
Figure 13B:
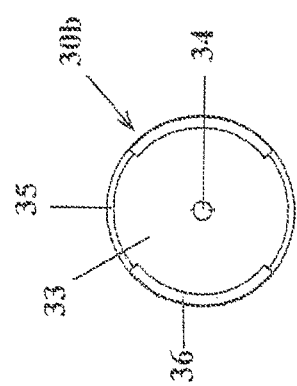
FIG. 13B is a front view of the ram extender shown in FIG. 13A.

As shown in FIG. 11, the syringe 70 includes a main cylindrical barrel 72 enclosing an inner volume 74 which in use of the syringe 70 is filled with contrast media or other solution or liquid to be dispensed through the distal end 76 of the syringe. At its distal end 76, the syringe 70 is provided with threading 78 in its interior surface, for connection of the distal end 76 of the syringe 70 to a catheter by means of luer-lock or other conventional coupling means.

The interior volume 74 of the syringe is bounded by an interior wall surface 80, as shown. At the proximal end 82 of the syringe is interiorly disposed a plunger 84 according to one embodiment of the present invention. The plunger 84 is of generally converging shape at its distal end, and includes an outer circumferentially continuous edge (side) surface 85 which contacts the inner wall surface 80 of the syringe. The plunger 84 further includes at least two diametrally opposed arrays of spaced-apart flexible resilient engagement members 86, as hereinafter more fully described.

At the proximal end of the syringe 70 on the exterior surface thereof are provided diametrally opposed flange or lug members 88 and 90, for engaging and locking the syringe to the adapter 10, as described below.

A first preferred embodiment of the ram extender 30a is illustrated in FIGS. 12A-12d. A second embodiment of ram extender 30 is illustrated in FIGS. 13A-13d. The ram extender 30a or 30b attaches to the ram of the injector 100. Depending on the model of the injector, one of the ram extenders 30a or 30b will be used. Before attaching either ram extender 30a or 30b, grippers or jaws 114 on the existing injector are removed from the drive ram. Ram extender 30a is attached to the drive ram via screws that are inserted through longitudinal apertures 32 in ram extender 30a and into threaded apertures in the front of the drive ram. Ram extender 30b is attached to the drive ram of the injector via a pin or other fastener that is inserted through transverse aperture 39 in the ram extender and through a transverse aperture (not shown) in the drive ram of the injector. Various other fasteners or means for attaching the ram extender 30a or 30b to the drive ram as are obvious to one of ordinary skill in the art are contemplated.

Figure 14:
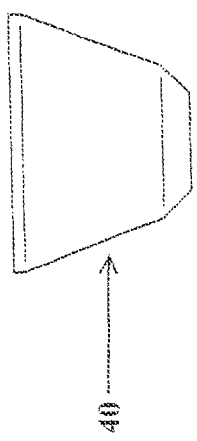
FIG. 14 is a side view of a ram tip cone.
Figure 16:
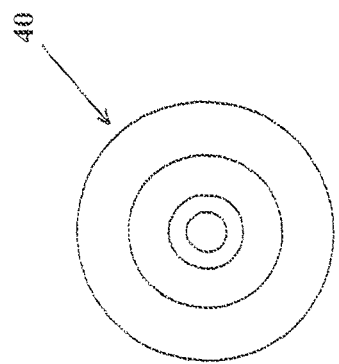
FIG. 16 is a front view of the ram tip cone shown in FIG. 14.
Figures 31, 32:
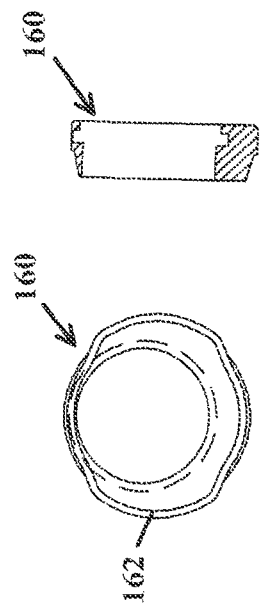
FIG. 31 is a top plan view of a further embodiment of a lifting ring.
FIG. 32 is a side cross-sectional view of the lifting ring of FIG. 31.
Figure 15:
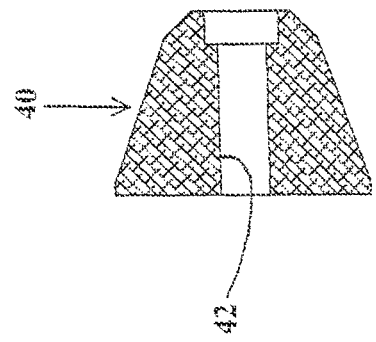
FIG. 15 is a side cross-sectional view of the ram tip cone shown in FIG. 14.

Ram extender 30a and 30b are of frustoconical shape, each having a front circular surface 33 with a central threaded aperture 34 that receives a fastener for attaching the ram tip cone 40 (See FIGS. 14-16) to the ram extender 30a or 30b. The ram extender 30a or 30b additionally has a frustoconical side surface 35 with rounded-over portions 36, a cylindrical body 37, and a rear connecting extension 38. Ram tip cone 40, as illustrated in FIGS. 14-16, attaches to front circular surface 33 via at least one fastener that is received within aperture 42 and into closed-ended threaded aperture 34 in ram extender 30a or 30b. Ram tip cone 40 provides a substantially complementary shape to the rear surface of plunger 84. With ram extender 30a, the ram tip cone 40 should be installed after the ram extender 30a is attached to the drive ram of the injector. With ram extender 30b, the user may attach ram tip cone 40 either before or after the ram extender 30b is attached to the drive ram of the injector.

As illustrated in FIGS. 17-22, lifting ring 60 has a cylindrical collar 64 which, in one embodiment, is constructed and arranged in a press fit relationship with lifting ring bounding wall 20 of the central bore 28 in the adapter body 12. The lifting ring may as shown in FIGS. 18, 20, and 22 include outwardly extending shoulder elements 62 that are diametrally opposite one another, so that the lifting ring has unshouldered circumferential portions that are diametrally opposite one another and that are between the shoulder elements 62. The flexible resilient engagement members 86 of the syringe plunger 84 may or may not engage the lifting ring shoulder elements 62, depending on the syringe's orientation relative to the adapter assembly 10. The outwardly deforming shoulder elements 62 of the lifting ring 60 radially outwardly deform the flexible resilient engagement members 86 of the plunger 84 so that the flexible resilient engagement members 86 thereby interact with the adapter to permit engagement of the plunger with the driving head upon rotation of the syringe relative to the adapter body 12 and lifting ring shoulders 62.

By the arrangement shown, the front-load syringe is rearwardly inserted with the flange members 88 and 90 engaging slots 14a in the adapter body 12 of syringe adapter assembly 10. After positioning in the slots 14a, the syringe is rotated about a center axis (ninety degrees, for example) to lockingly engage flange members 88 and 90 with the internal grooves 27 and 29 communicating with the slots 14a and forming a retention flanges 23 and 25 transverse to the direction of slot 14a.

Such engagement of the syringe 70 with adapter assembly 10 causes the flexible resilient engagement members 86 to be spread by shoulder elements 62 of the lifting ring 60 so that the frustoconical side surface 35 of the ram extender 30a or 30b then engages the flexible resilient engagement members 86 upon the rotation of the syringe. The plunger 84 of the syringe is thereby coupled to the ram extender 30a or 30b. Upon installation of the syringe, the ram extender 30a or 30b is thereby subsequently forwardly driveable to advance the plunger in the syringe and effect delivery of contrast medium to the patient.

The syringe plunger 84, after such advancement to the distal end of the interior passage in the syringe barrel, may be uncoupled from the catheter or patient line connected to the distal end of the syringe. Thereafter the plunger is retractable in the interior passage of the syringe barrel. Once the plunger is fully retracted, the syringe and plunger may be rotated approximately ninety degrees to contact the flexible resilient engagement members 86 again with the shoulders 62 of the lifting ring, thereby spreading the flexible resilient engagement members 86 so that the plunger can be disengaged from the ram extender 30a or 30b by forward translational movement of the syringe relative to the adapter assembly 10.

Thus, when the flexible resilient engagement members 86 are contacted with the shouldered portions 62 of the lifting ring, they are spread radially outwardly, and when the flexible resilient engagement members 86 overlie the unshouldered portions of the lifting ring 60, such members 86 are in a retracted state for engagement with the frustoconical side surface 35 of the ram extender 30a or 30b with the attached ram tip cone 40.

Figure 23:
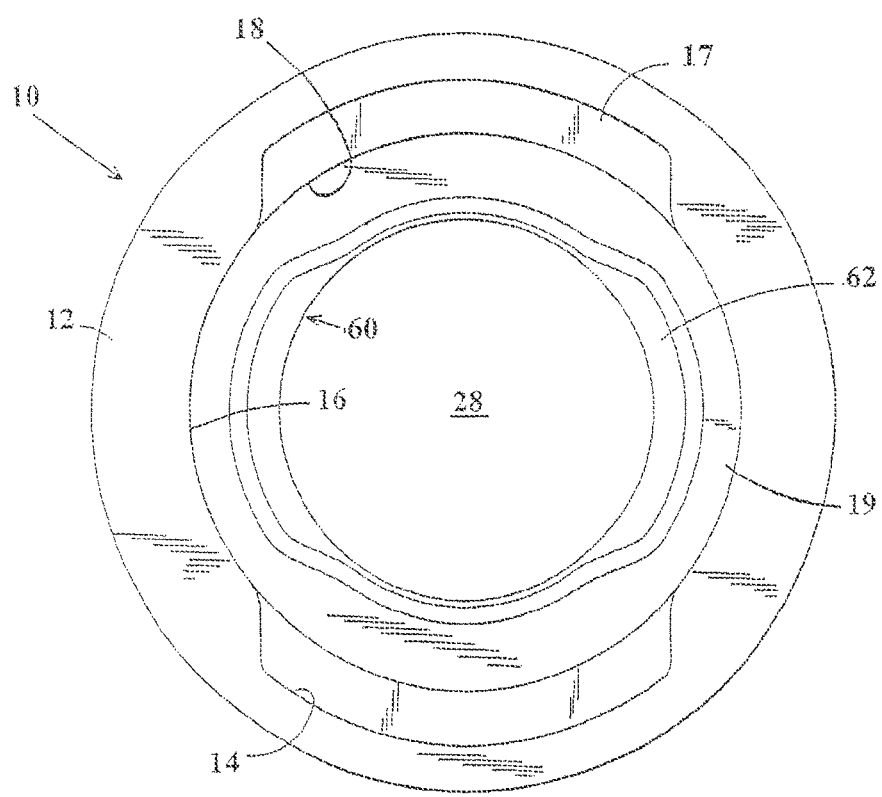
FIG. 23 is a front elevational view of the syringe adapter assembly, with installed lifting ring.

FIG. 23 is a front elevation view of the adapter 10 and lifting ring 60, wherein the corresponding structural elements of the adapter are numbered identically. While the lifting ring 60 is shown and described as press fitted into the adapter 10, those skilled in the art will recognize the adapter and lifting ring 60 could be integrally formed as a single component. The lifting ring 60 may be suitably constructed to be of varying form, and may be constructed as shown in FIGS. 17-22, with diametrally opposed lifting shoulder elements, or alternatively with a circumferentially continuous shoulder element.

The adapter assembly 10 is attached to the injector 100 via the adapter connector plate 50, illustrated in FIGS. 24-26. With additional reference to FIG. 33, to install the adapter 10 onto the injector of, e.g., FIGS. 1-3, door 102 is opened and the pressure jacket 106 and rotating cam assembly 104 are both removed from the injector. Thereinafter, the adapter connector plate 50 is fitted into the circular recess 112 in the back of door 102, which was occupied by the rotating cam assembly 104. Extensions 56 likewise fit into recesses 116 in the back of the door, ensuring that the connector plate 50 is oriented in one of only two possible positions, which are 180-degrees apart. In other words, the connector plate 50 is keyed with the recess 112 so that the connector plate can only be inserted with the recess 112 in one of two orientations. As can be seen in FIG. 24, the adapter connector plate 50 additionally has a plurality of apertures 52. In a preferred embodiment, the adapter connector plate has three apertures 52 arranged in a isosceles or other non-equilateral triangular orientation, such that the adapter body 12 can only be mounted in one orientation relative to the connector plate.

With the adapter connector plate 50 located in slot 112, the rear extension 24 of adapter body 12 is inserted into the door 102 from the opposite, i.e., front side of the door. As can be seen in FIG. 10, the rear portion of the adapter body 12 comprises a plurality of threaded apertures 26 that correspond when positioned properly to apertures 52 in adapter connector plate 50. Thus, threaded apertures 26 and 52 are aligned such that the user inserts screws (not shown) through apertures 52 in the adapter connector plate 50 and through threaded apertures 26 in the rear of the adapter body 12. This limited orientation of the connector plate 50 relative to the door 102, and of the adapter body 12 relative to the connector plate 50, ensures that the adapter assembly will be installed in one of two alternate orientations relative to the injector 100 each time, the orientations being 180 degrees apart. The connector plate 50 does not inhibit the action of door 102, which is returned to its closed position for operation.

In operation, to install adapter assembly 10 onto the '031 injector, the user first opens and rotates door 102 counterclockwise to remove the door 102 from the injector 100. Next, the rotating cam assembly 104 is removed from its slot 112 in the back of the door 102, by removing the associated screws. The pressure jacket retaining screws are removed, and the pressure jacket 106 is removed from door 102.

To install adapter assembly 10, the user inserts connector plate 50 into slot 112 in the rear surface of door 102. Adapter body 12 is inserted into front face of door 102, and apertures 26 in the rear cylindrical extension 24 are aligned with apertures 52 in the connector plate 50. The adapter body 12 and connector plate 50 are then secured to the door 102 by fasteners through apertures 50 and 26.

The grippers 114 are removed from the drive ram of the injector 100 by removing the fastening means. Depending on the model of the injector, the grippers 114 are secured to the drive ram by either longitudinal screws or by a transverse pin. After the grippers 114 are removed, the ram extender 30*a* or 30*b* of the present invention is secured to the drive ram. Ram extender 30*a* is secured to the drive ram by screws inserted through apertures 32 and into corresponding threaded apertures in the front surface of the drive ram. Ram extender 30*b* is secured to the drive ram by transverse pin that is inserted through the transverse aperture in the drive ram and through aperture 39 in ram extender 30*b*. Finally, the ram tip cone 40 may be installed the front circular surface 33 of the ram extender 30*a* or 30*b* by a screw inserted through aperture 42 in ram tip cone and into threaded aperture 34 in the ram extender 30*a* or 30*b*. The adapter assembly 10 is removable by reversing the foregoing steps, so that the original OEM parts can be replaced.

Figure 29:
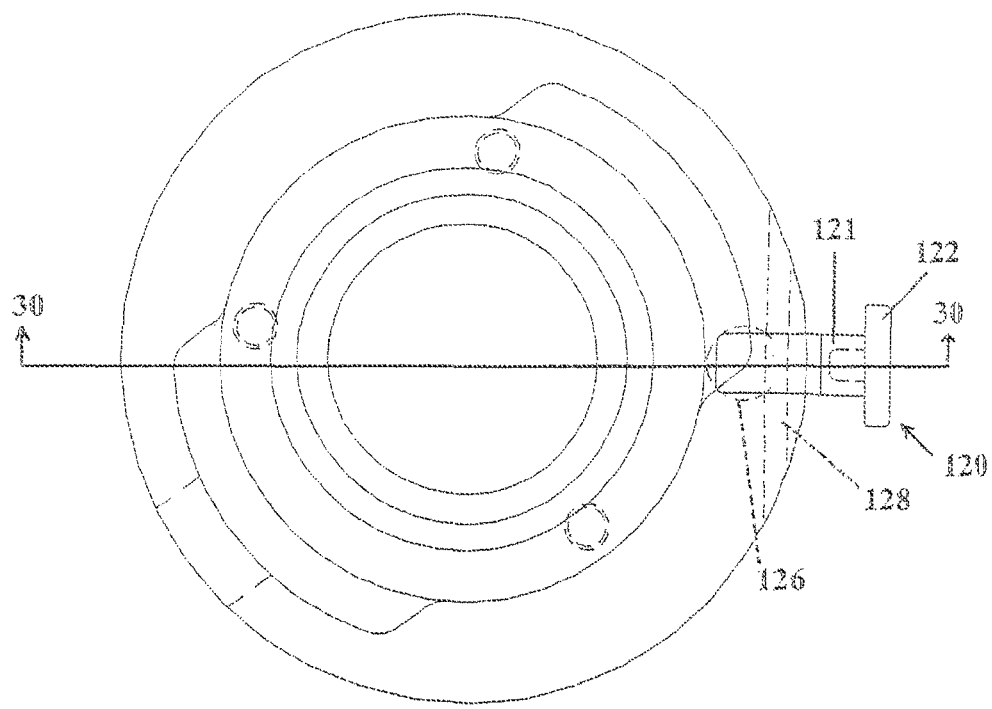
FIG. 29 is a front view of a further embodiment of a syringe adapter body.
Figure 30:
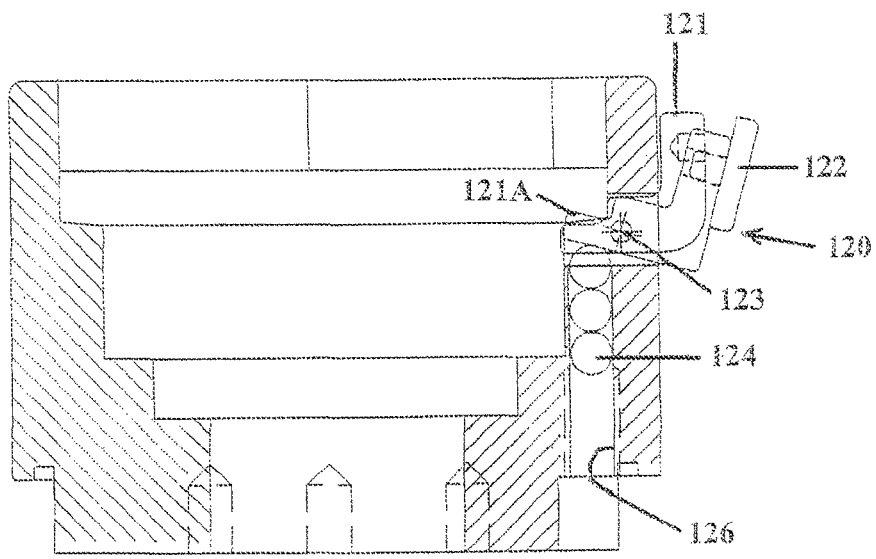
FIG. 30 is a cross-sectional view of the syringe adapter body of FIG. 29, taken along line 30-30.

A further embodiment of an adapter body, an example of which is shown in FIGS. 29-30, comprises a syringe lock that prevents a syringe that is installed in the adapter body 12 from rotating in the uninstall direction. The syringe lock may generally comprise a detent or protrusion that is fixed or normally urged into the path of a portion of the syringe, e.g., forwardly from shoulder 17 near an inbound end of one of the diametrically opposed grooves 27, 29. The detent may be biasable out of the rotational travel path of flange 88 or 90 when the syringe is inserted into the adapter body 12 and rotated in the install direction. After the syringe is rotated and flanges 88, 90 are secured within grooves 27 and 29, detent 120 again is urged forwardly from shoulder 17, which substantially prevents unwanted rotation of the syringe, and thus locks the syringe relative to the adapter body 12 until removal is desired.

One embodiment of a syringe lock 120 is illustrated in FIGS. 29-30. Syringe lock 120 comprises generally L-shaped lock body 121 that rotates about an axis formed by pin 123 that is housed in aperture 128. Lock body 121 may have tab 122 attached to facilitate ergonomic user actuation of syringe lock 120.

As illustrated in FIG. 30, the interior portion of lock body 121 is generally urged forwardly via biaser 124. Biaser 124 may comprise any of a plurality of structures known in the art. For example, biaser 124 may comprise one or more resilient members that are attached to, or rearwardly adjacent to the lock body 121 and are compressible when an appropriate rearward force is applied to the interior portion of lock body 121 and resiliently return to the original position when the force is removed. Additionally, biaser 124 may comprise a spring or any of a plurality of similar compressible structures known in the art.

As shown in FIG. 28, biaser 124 may be housed in aperture 126. Aperture 126 is preferably at least partially open on its forward end and closed or closable on its rearward end by a frictionally-engaged plug or set screw (not shown), or any of a plurality of structures or sealing methods as are known in the art.

As illustrated in FIG. 28, a preferred embodiment of the syringe lock comprises a detent or protrusion that may be ramped or angled on the inbound side to enable the syringe flange 88 or 90 to urge the syringe lock out of the path of the syringe flange when installing the syringe. For example, the inbound, i.e., side of the detent that the syringe contacts upon installation of the syringe, may be angled 10-45 degrees, although it should be appreciated that greater the detent protrudes in the rotational path of the syringe, the more angle of the inbound side ramp may be increased, up to a maximum angle. It is also contemplated that the opposite or outbound side of the syringe lock detent may not similarly ramped or angled, so that the syringe flange 88 or 90 cannot be rotated in the uninstall direction without the user depressing tab 122 and biasing the detent rearwardly. It is also contemplated that the syringe lock detent may be manually actuated from an unlocked or unblocked position to a locked or blocked position. Any means known in the art, such as an over center mechanism, may be utilized to provide such a two-way manually actuated detent.

Further embodiments for a syringe lock are contemplated, including a fixed (non biasing) protrusion of a preselected size and shape that is located in the rotational path of the syringe. Additionally, the syringe lock may comprise a detent that is manually actuated and fixable in both an on and off state. Furthermore, the syringe lock may comprise a detent that is urged in the rotational path of the syringe, yet automatically biasable out of the path of the syringe in both an install and uninstall directions. Finally, any embodiment of the syringe lock, rather than being located on an adapter that is attachable to an injector, may be installed or be manufactured directly on the injector itself.

The syringe lock mechanism aids in preventing malfunction of the injector by insuring that the syringe is fully installed in the adapter before actuation of the injector. Misaligned or partially installed syringes may concentrate forces in certain areas of the syringe, including mounting flanges, and using misaligned or partially installed syringes is more likely to result in spillage of fluid from the syringe.

The forgoing disclosure is illustrative of the present invention and is not to be construed as limiting thereof. Although one or more embodiments of the invention have been described, persons of ordinary skill in the art will readily appreciate that numerous modifications could be made without departing from the scope and spirit of the disclosed invention. As such, it should be understood that all such modifications are intended to be included within the scope of this invention. The written description and drawings illustrate the present invention and are not to be construed as limited to the specific embodiments disclosed.

What is claimed is:

1. A method of locking a syringe relative to a front-loadable power injector, the method comprising the steps of:
   providing a syringe having mounting flanges proximate to a rear end of the syringe;
   providing a front-loadable injector including an adapter having a syringe receiving opening and a pair of retaining flanges adapted to engage the syringe mounting flanges upon rearward insertion of the syringe within the opening and rotation of the syringe;
   providing a syringe lock in a rotational path of the syringe, the syringe lock protruding from an exterior of the adapter through the adapter and into the syringe receiving opening; and,
   installing a syringe relative to the injector by engaging the syringe mounting flanges with the retaining flanges.

2. The method of claim 1 further comprising actuating the syringe lock by rotating the syringe.

3. The method of claim 1 further comprising manually actuating the syringe lock.

4. The method of claim 1, where the syringe lock includes a detent.

5. The method of claim 4, where the detent is normally present in a rotational path of a syringe and is movable out of the rotational path of the syringe.

6. The method of claim 5, where an inbound side of the detent is ramped to enable the syringe to move the detent out of the rotational path of the syringe when installing the syringe.

7. The method of claim 6, where an outbound side of the detent is ramped to enable the syringe to move the detent out of the rotational path of the syringe when uninstalling the syringe.

8. The method of claim 6, where an outbound side of the detent is unramped to preclude the syringe from moving the detent out of the rotational path of the syringe when uninstalling the syringe.

9. The method of claim 4, where the detent is fixed.

10. The method of claim 4, where the syringe lock includes a lever having an interior portion forming the detent, and an exterior portion forming a handle for manually biasing the detent.

11. The method of claim 4, where the adapter further comprises an axially extending aperture extending forwardly from the rear end of the adapter and a least partially open to a rotational path of the syringe adjacent to the detent, where the aperture houses a biaser that urges the detent into a rotational path of a syringe.

12. The method of claim 11, where the biaser comprises a spring.

13. The method of claim 11, where the biaser comprises at least one resilient member.

* * * * *